US012447084B2

(12) United States Patent
Susec

(10) Patent No.: US 12,447,084 B2
(45) Date of Patent: Oct. 21, 2025

(54) INTUBATION BARRIER BOX

(71) Applicant: Otto C. Susec, Chandler, IN (US)

(72) Inventor: Otto C. Susec, Chandler, IN (US)

( * ) Notice: Subject to any disclaimer, the term of this patent is extended or adjusted under 35 U.S.C. 154(b) by 1099 days.

(21) Appl. No.: 17/095,246

(22) Filed: Nov. 11, 2020

(65) Prior Publication Data

US 2021/0353481 A1 Nov. 18, 2021

Related U.S. Application Data

(60) Provisional application No. 63/026,018, filed on May 16, 2020.

(51) Int. Cl.
*A61G 10/00* (2006.01)
*A61B 46/00* (2016.01)
*A61B 90/40* (2016.01)

(52) U.S. Cl.
CPC ............ *A61G 10/005* (2013.01); *A61B 46/00* (2016.02); *A61B 90/40* (2016.02)

(58) Field of Classification Search
CPC ............... A61M 21/0094; A61H 33/14; A61H 2033/141-148; A62B 31/00; A62B 29/00; A61B 90/05; A61B 90/40; A61B 2090/401
See application file for complete search history.

(56) References Cited

U.S. PATENT DOCUMENTS

| | | | | |
|---|---|---|---|---|
| 10,967,204 B1 * | 4/2021 | Adams | A61G 10/023 | |
| 2007/0094798 A1 * | 5/2007 | Yu | A61G 13/10 | 5/507.1 |
| 2008/0210239 A1 * | 9/2008 | Lewis | A62B 31/00 | 128/205.26 |
| 2021/0315758 A1 * | 10/2021 | Bui | A61G 10/02 | |
| 2021/0322242 A1 * | 10/2021 | Hogan | A61G 10/023 | |
| 2021/0330918 A1 * | 10/2021 | Menezes | A61G 10/005 | |
| 2021/0353482 A1 * | 11/2021 | Bardo | A61G 10/005 | |
| 2022/0110711 A1 * | 4/2022 | Vizulis | A61G 10/005 | |
| 2023/0130301 A1 * | 4/2023 | Spiller | A61G 10/005 | 600/21 |
| 2023/0149120 A1 * | 5/2023 | Knezek | A61M 16/0003 | 128/846 |

* cited by examiner

*Primary Examiner* — Thaddeus B Cox

(74) *Attorney, Agent, or Firm* — MIP Legal, Ltd.; Bryce D. Miracle, Esq.

(57) ABSTRACT

A transparent intubation barrier in the form of a box is provided which substantially reduces aerosol exposure and the transmission of disease between patient and healthcare provider.

14 Claims, 11 Drawing Sheets

INTUBATION BARRIER BOX

CROSS-REFERENCE TO RELATED APPLICATION

This application is based upon and claims the priority filing date of the previously filed, copending U.S. Provisional patent application entitled "INTUBATION BARRIER BOX" filed May 16, 2020, Ser. No. 63/026,018, the entire disclosure of which is hereby incorporated herein by reference.

FIELD OF THE INVENTION

The present disclosure relates to an apparatus for providing a barrier shield between a patient and a healthcare provider. More specifically, the present disclosure relates to an intubation box configured to enclose the patient's head, face, and neck, thereby reducing the spread of infectious diseases while undergoing a medical procedure.

BACKGROUND

Despite the availability of personal protective equipment (PPE), medical providers have been compelled to improvise protective barrier enclosures to protect from potentially dangerous aerosol exposure during high-risk procedures such as endotracheal intubation and extubation. As an adjunct to standard PPE, a transparent barrier enclosure reduces exposure from any potentially aerosolized chemicals and/or biohazards during any head, face, neck, oropharyngeal and/or airway procedures (not limited to intubation, extubation, crycothyroidotomy, laceration repairs, abscess incision & drainage, etc.).

Currently, transparent barriers may be provided in the form of a box having an interior that is made accessible to providers' upper extremities through multiple open portals that are integral to its functionality. Although theoretically much reduced, these portals still allow for potential aerosol exposure.

For the foregoing reasons, there is a need for a transparent barrier that substantially reduces aerosol exposure and the transmission of diseases and other biohazards.

SUMMARY

In accordance with a version of the invention, an improved transparent intubation barrier in the form of a box is provided which substantially reduces aerosol exposure and the transmission of disease between patient and healthcare provider.

The intubation barrier is optimally configured to allow the operator to efficiently access the patient's head and neck comfortably, given the inherent limitations of fixed access portals in any combination of specific size, shape, and spacing. In addition, significant consideration has been made to conceal only the area patient's head and neck down to approximately the top of the shoulders for several reasons: (1) the full range of motion of the upper extremities has been made available to nursing; (2) increase eligibility for use of the box in patients with extremely tall chest girths and/or with very wide shoulders; and (3) leaving the anterior precordium/chest exposed in those instances of cardiac arrest where chest compressions and/or electrical cardioversion might be indicated.

In certain versions of the application, the intubation barrier generally comprises a front operator panel including a left side operator arm portal and a right side operator arm portal, wherein each of the left side and right side operator arm portals support an iris type diaphragm operably closing each portal in the absence of an arm. Further, the intubation barrier may include a rear patient panel having a patient portal providing an arcuate bottom perimeter forming a patient entrance for positioning the upper chest of the patient therein.

In certain versions of the application, a left side panel and right side panel is provided. Each of the left side and right side panels includes respective left side and right side assistant arm portals supporting an iris-type diaphragm operably closing each portal in the absence of an arm.

Further, a top roof panel is provided, extending between the rear patient panel and the left and right side panels. Additionally, an angled front view panel extends between the front operator panel and the top roof panel. The plane of the angled front view panel is positioned at an angle relative to the top roof panel and the front operator panel.

In specific versions of the intubation barrier, at least one of the arm portals includes at least two adjacent flexible sheet inserts, each having a plurality of radial divides emanating from a center and equidistant from the others. The radial divides of the first flexible sheet insert are operably positioned offset from the radial divides of the second flexible sheet insert.

In yet other versions of the application, a removable support frame is operably positioned to support the adjacent flexible sheet inserts between the interior surface of the removable support frame and the exterior surface of the respective side panel forming an enclosure over the portal, thereby allowing the flexible sheet inserts to be replaced and cleaned.

In a version of the intubation barrier, the rear patient panel may provide an attachment perimeter and a removable support frame. The removable support frame is operably positioned to support the perimeter of the patient portal between the interior surface of the support frame and the attachment surface of the attachment perimeter. A plurality of knob screws may be used to secure the removable support frame to the attachment perimeter.

In another version of the application, the arcuate bottom perimeter of the patient portal may include a series of flaps formed between radial divides, thereby allowing the bottom perimeter to expand and seal over the chest of the patient.

In a preferred version, the patient portal comprises of at least two adjacent flexible sheet inserts, wherein the arcuate bottom perimeter of each flexible sheet insert includes a series of flaps formed between radial divides. The flaps of the first flexible sheet insert are operably positioned offset from the flaps of the second flexible sheet insert.

These and other features of the present invention will become readily apparent upon further review of the following specification and drawings.

BRIEF DESCRIPTION OF THE DRAWINGS

These and other features, aspects, and advantages of the present invention will become better understood with regard to the following description and accompanying figures where.

DETAILED DESCRIPTION

In the following description, for purposes of explanation and not limitation, specific details are set forth such as particular architectures, interfaces, techniques, etc. in order to provide a thorough understanding of the present invention. However, it will be apparent to those skilled in the art that the present invention may be practiced in other versions that depart from these specific details. In other instances, detailed descriptions of well-known devices, circuits, and methods are omitted so as not to obscure the description of the present invention with unnecessary detail.

Moreover, the description is not to be taken in the limiting sense but is made merely for the purpose of illustrating the general principles of the invention, since the scope of the invention is best defined by the appended claims. Various inventive features are described below that can each be used independently of one another or in combination with other features.

Unless otherwise defined, all technical terms used herein have the same meaning as commonly understood by one of ordinary skill in the art to which the invention belongs. As used in the specification and the appended claims, the singular forms "a," "an," and "the" include plural references unless the context clearly dictates otherwise. Any reference to "or" herein is intended to encompass "and/or" unless otherwise stated.

Doctors may be defined as Operators herein. Respiratory therapist, nurse(s) and/or technicians(s) may be defined by "Assistants" herein. Both Operators and Assistants collectively may be defined as medical/healthcare providers herein.

Figure 1:
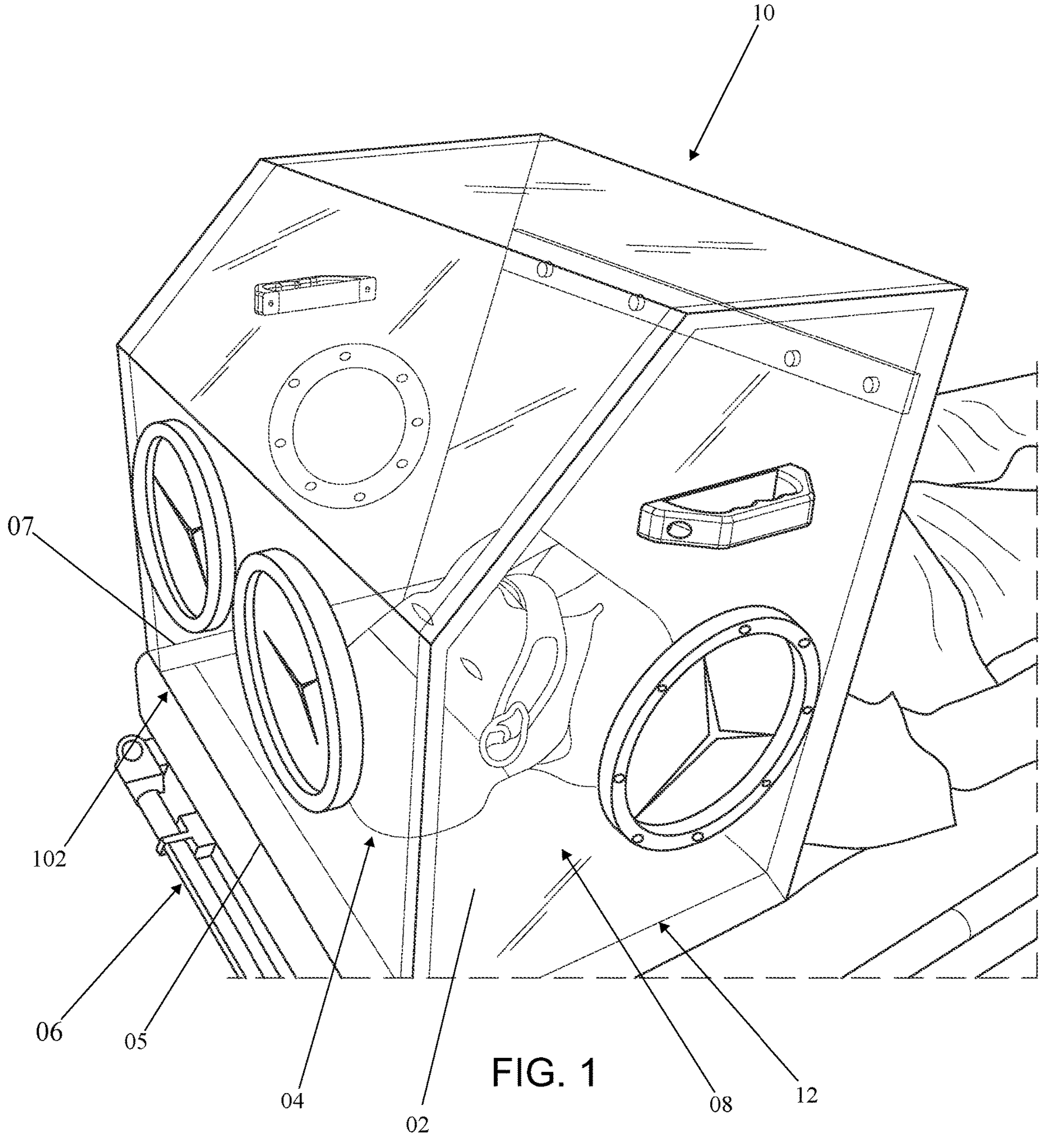
FIG. 1 is a front perspective view of a version of the intubation barrier shown while positioned over the head, neck, and shoulders of a patient.

With reference to the figures, a description of a version of the invention will be provided and is generally designated as numeral 10. Generally speaking and as best illustrated in FIG. 1, the application is directed towards a transparent intubation barrier 10 defining an interior cavity 08 having an open bottom 12 which is placed over the head, neck and shoulder of a patient 04 laying on a hospital bed 06, sealing the patient 04 within the cavity 08 and the top surface 02 of the hospital bed 06. Generally, during a procedure, the Operators are positioned at the head of the bed 06 or forward of the intubation barrier 10 and the Assistants are positioned laterally to the sides of the bed 06 and intubation barrier 10.

Figure 2:
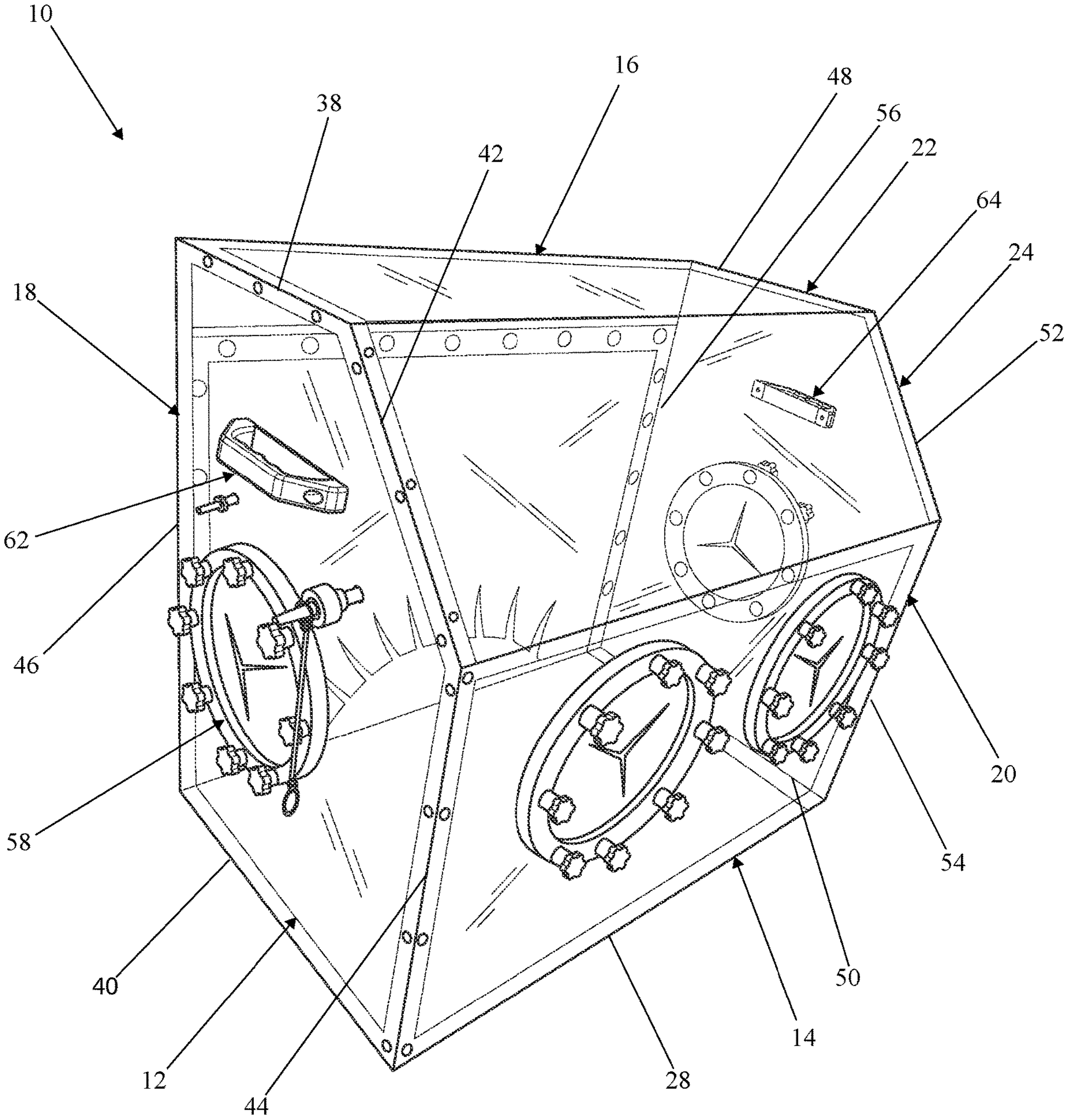
FIG. 2 is a left perspective view of the version shown in FIG. 1.
Figure 3:
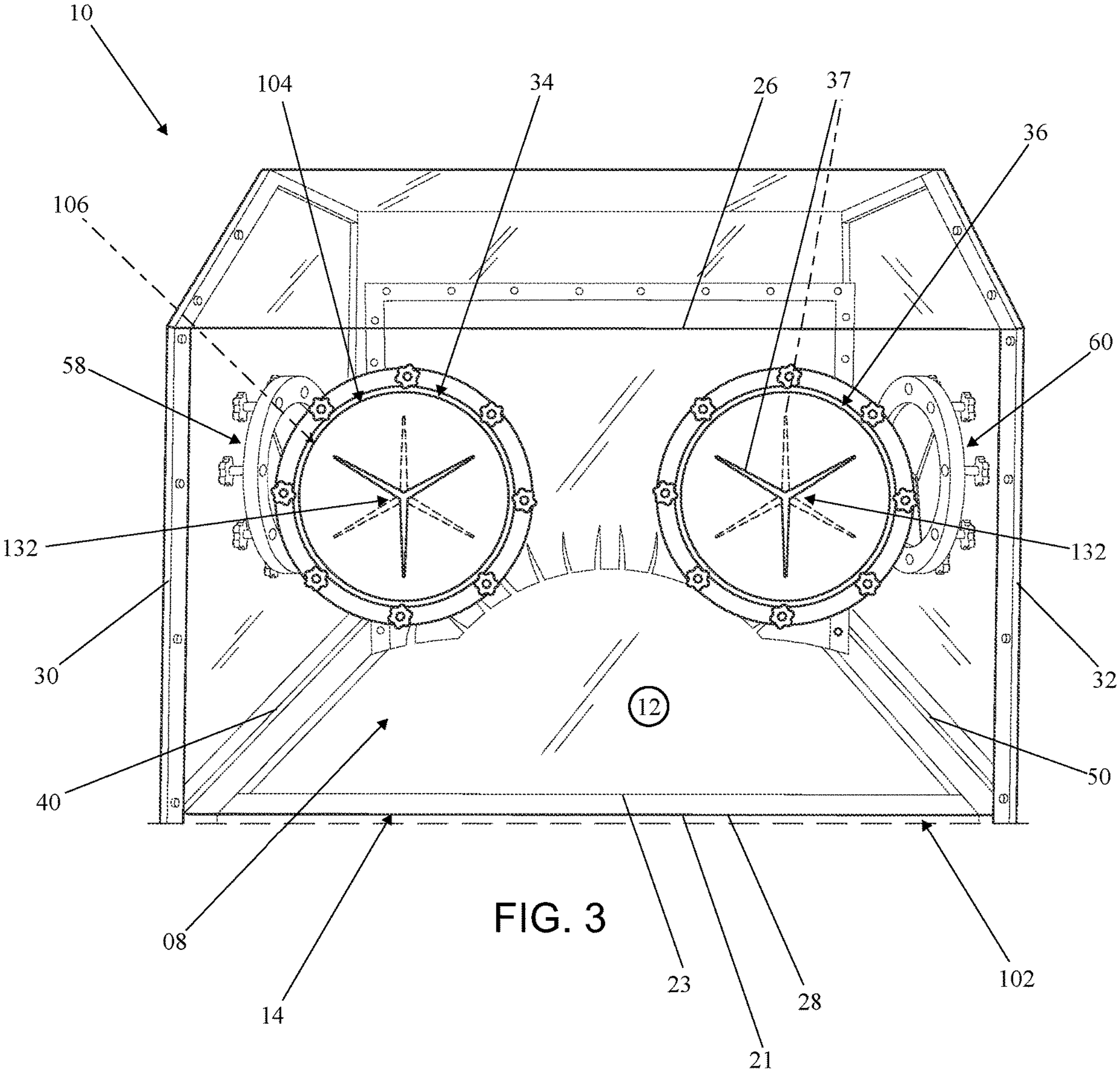
FIG. 3 is a front elevation view of the version shown in FIG. 1.
Figure 4:
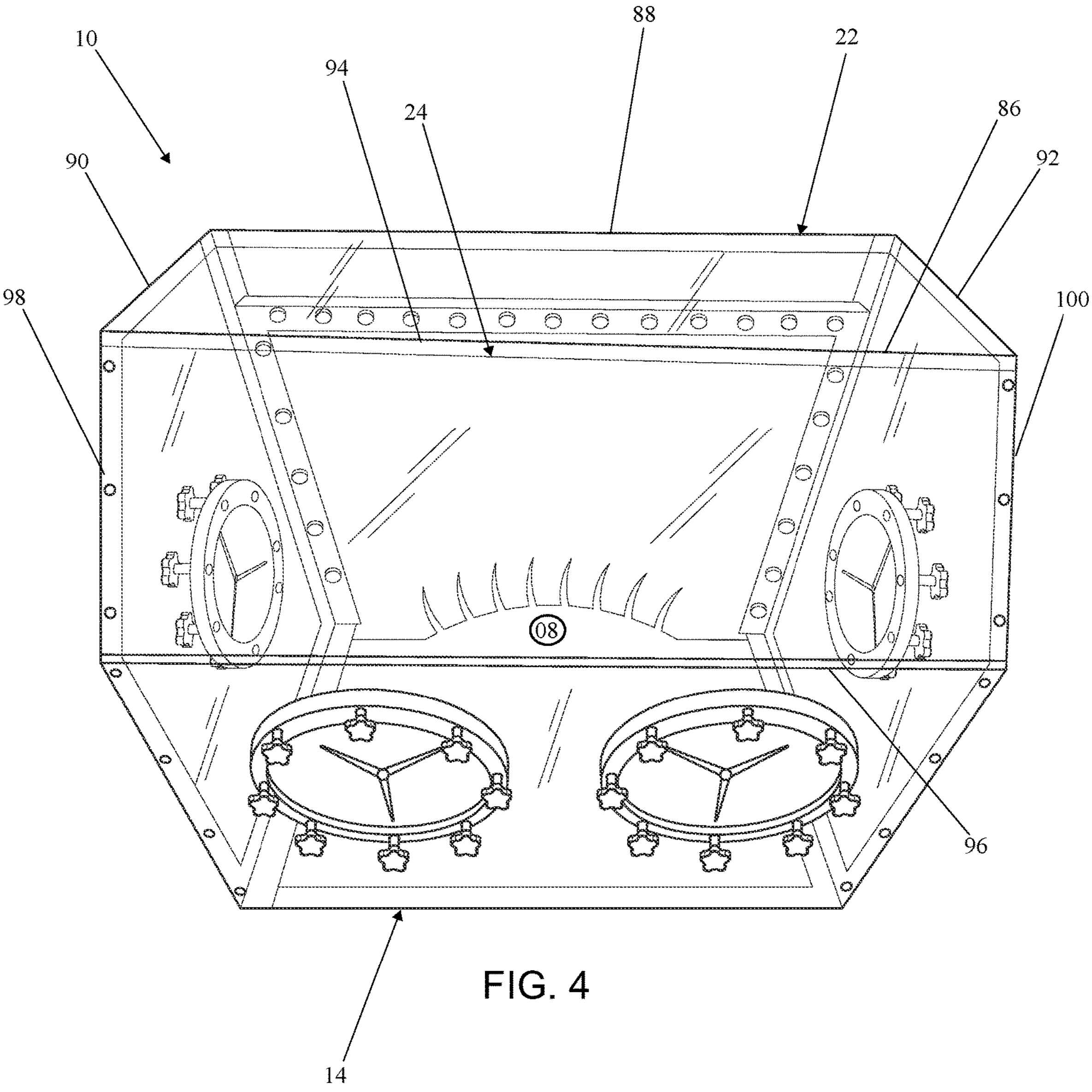
FIG. 4 is a top-down perspective view of the version shown in FIG. 1.

With reference to FIG. 2-FIG. 4, the intubation barrier 10 generally comprises a plurality of transparent panels which collectively form a box-like structure forming the open bottom 12 and providing support for a removable rear patient panel 16. In a specific version of the application, the intubation barrier 10 comprises a front operator panel 14, a rear patient panel 16, a left and right side panels 18, 20, a top roof panel 22, and an angled front view panel 24.

Referring to FIG. 3, the front operator panel 14 is generally configured to provide the operator access to the patient 04 during a procedure. The front operator panel 14 is operably positioned forward of the patient's head and parallel with the top perimeter 05 of the hospital bed 06 while in use (see FIG. 1). In the version, the front operator panel 14 has a top edge 26, a bottom perimeter 28, and opposing left and right side edges 30, 32 which form a rectangular panel positioned perpendicular to the longitudinal axis of the patient 04 or hospital bed 06. The front operator panel 14 further includes a left side and right side operator arm portals 34, 36 which allow the operator access to the cavity 08 by way of inserting their hands and arms therethrough respectively. Preferably, the front operator panel 14 has a height between 13"-19" inches, preferably 16" and a width of 24"-31", preferably 27.5".

As best illustrated in FIG. 2, the left side and right side panels 18, 20 are generally configured to provide access to the assistants during a procedure. While in use, the left side and right side panels 18, 20 are aligned in parallel with the longitudinal axis of the patient 04 and the side edge 07 of the bed 06 (See FIG. 1). The left side panel 18 has a top edge 38, a bottom perimeter 40, an angled edge 42 and opposing front and rear side edges 44, 46. Reciprocally, the right side panel has a top edge 48, a bottom perimeter 50, an angled edge 52 and opposing front and rear side edges 54, 56. The left side edge 30 of the front operator panel 14 and the front edge 44 of the left side panel 18 form a left, front edge of the intubation barrier 10. Correspondingly, the right side edge 32 of the front operator panel 14 and the front edge 46 of the right side panel 20 form a right, front edge of the intubation barrier 10. Preferably, the left side and right side panels 18, 20 have an overall height of between 21"-25", preferably 23" and a width of 14"-19", preferably 16.5".

Figure 6:
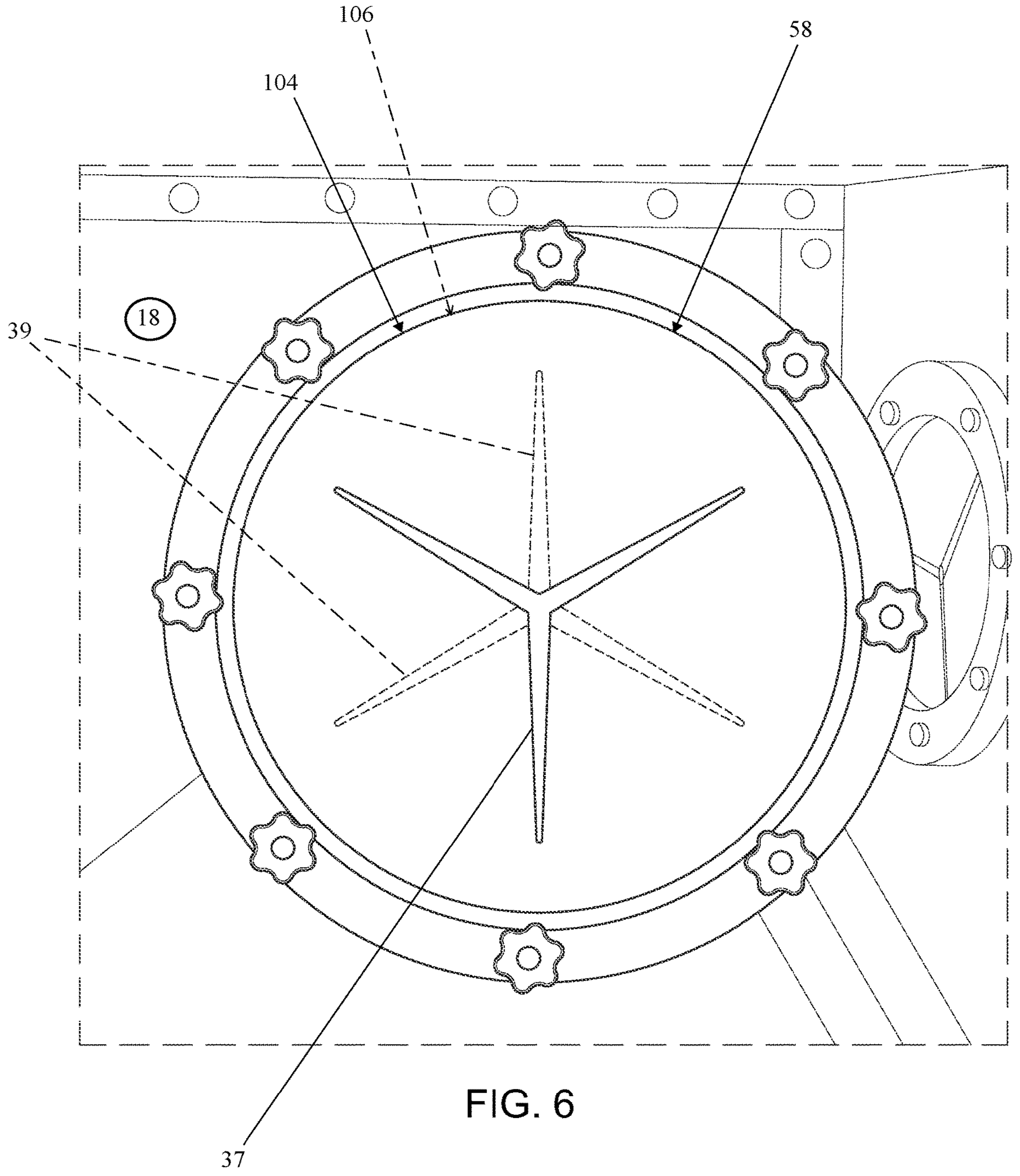
FIG. 6 is an up-close view of an operator arm portal of the version shown in FIG. 1.
Figure 7:
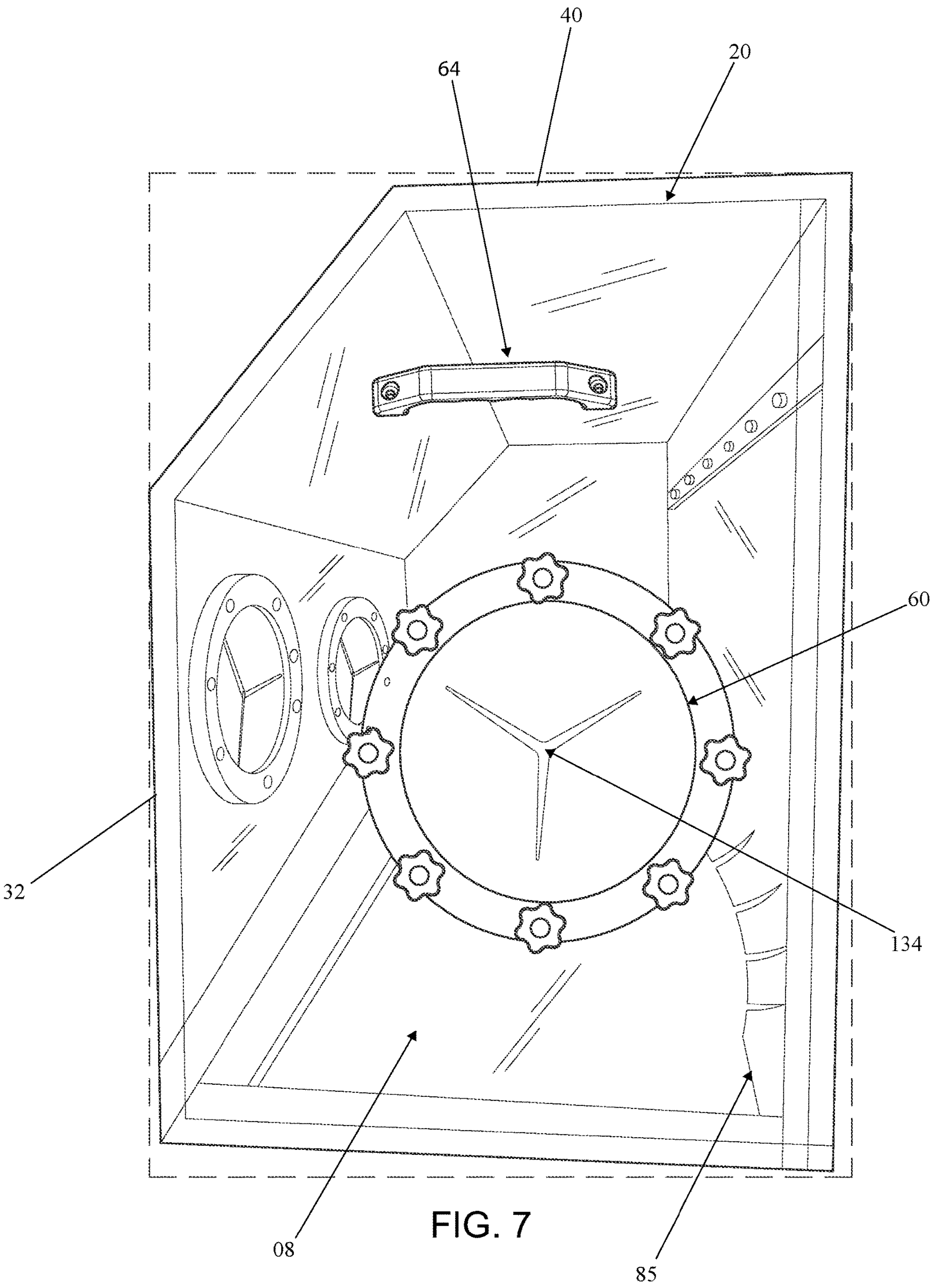
FIG. 7 is a right side elevation view of the version shown in FIG. 1.

As best shown in FIG. 6 and FIG. 7, the left side panel 18 includes a left side assistant arm portal 58 and the right side panel 20 includes a right side assistant arm portal 60 which allow the operator and assistant access to the cavity 08 by placing their hand and arm therethrough from the side of the patient's bed 06. Further, in certain versions, the left side and right side panels 18, 20 each have a left side and right side handle 62, 64 for ease of transport, positioning, moving, and removal of intubation barrier 10.

As best shown in FIG. 1, FIG. 8, FIG. 9, and FIG. 11, the rear patient panel 16 is generally configured to envelope or mold over the upper torso of various patient dimensions—thereby sealing off the cavity 08 and encapsulating the patient's head, neck, and shoulder therein (See FIG. 1). The rear patient panel 16 includes a top edge 66, a bottom perimeter 68, and opposing left and right side edge 70, 72. In the version, the rear patient panel 16 generally comprises a top portion 74 and a lower flexible patient portal 76 extending below the top portion 74 terminating at the bottom perimeter 68 defining a patient entrance 78 for positioning over the patient upper chest. Preferably, the rear patient panel 76 has an overall height between 20"-26", preferably 23" and a width of 24"-31", preferably 27.5".

Figure 8:
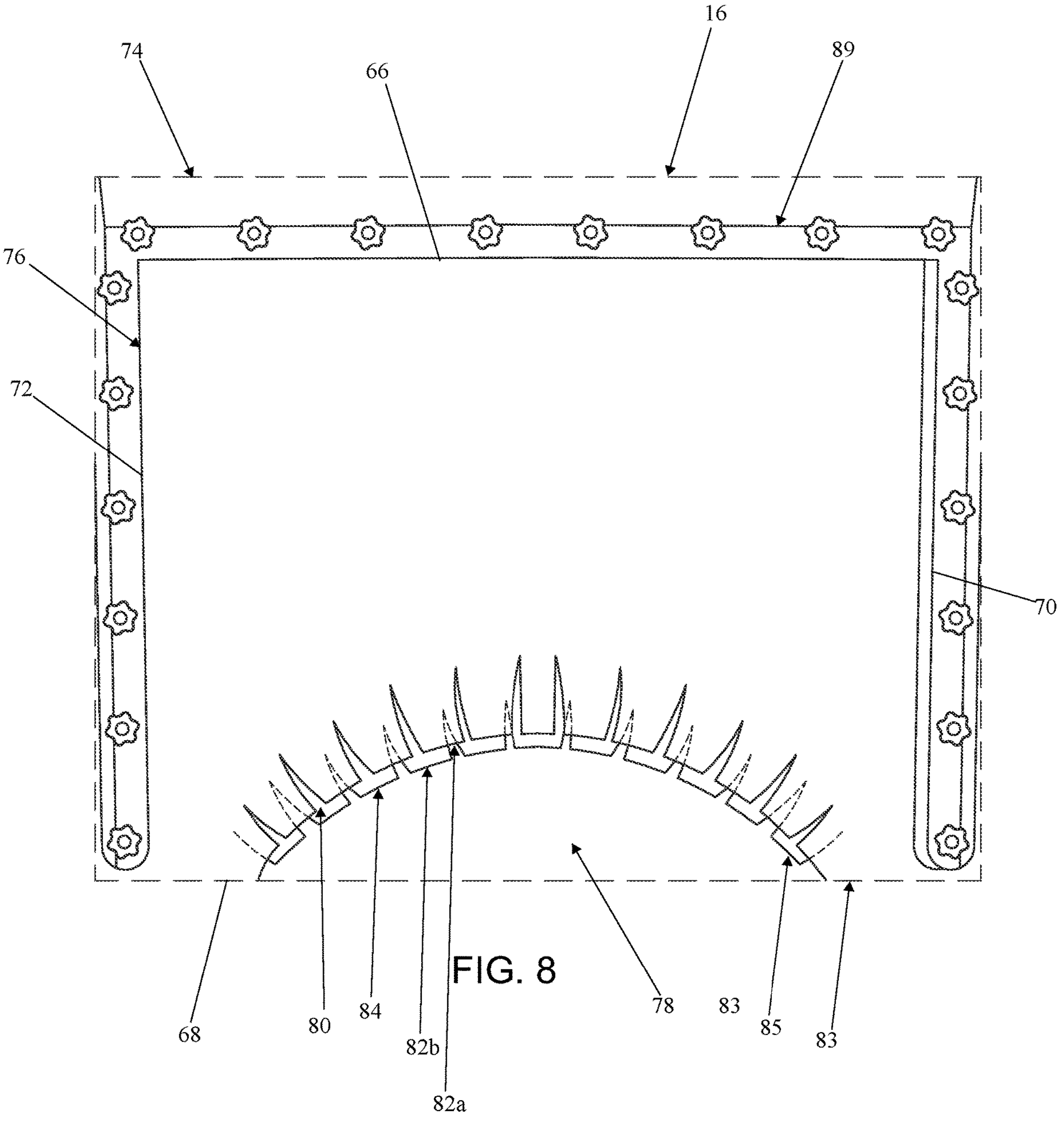
FIG. 8 is a rear elevation view of the rear patient portal of the version shown in FIG. 1.
Figure 9:
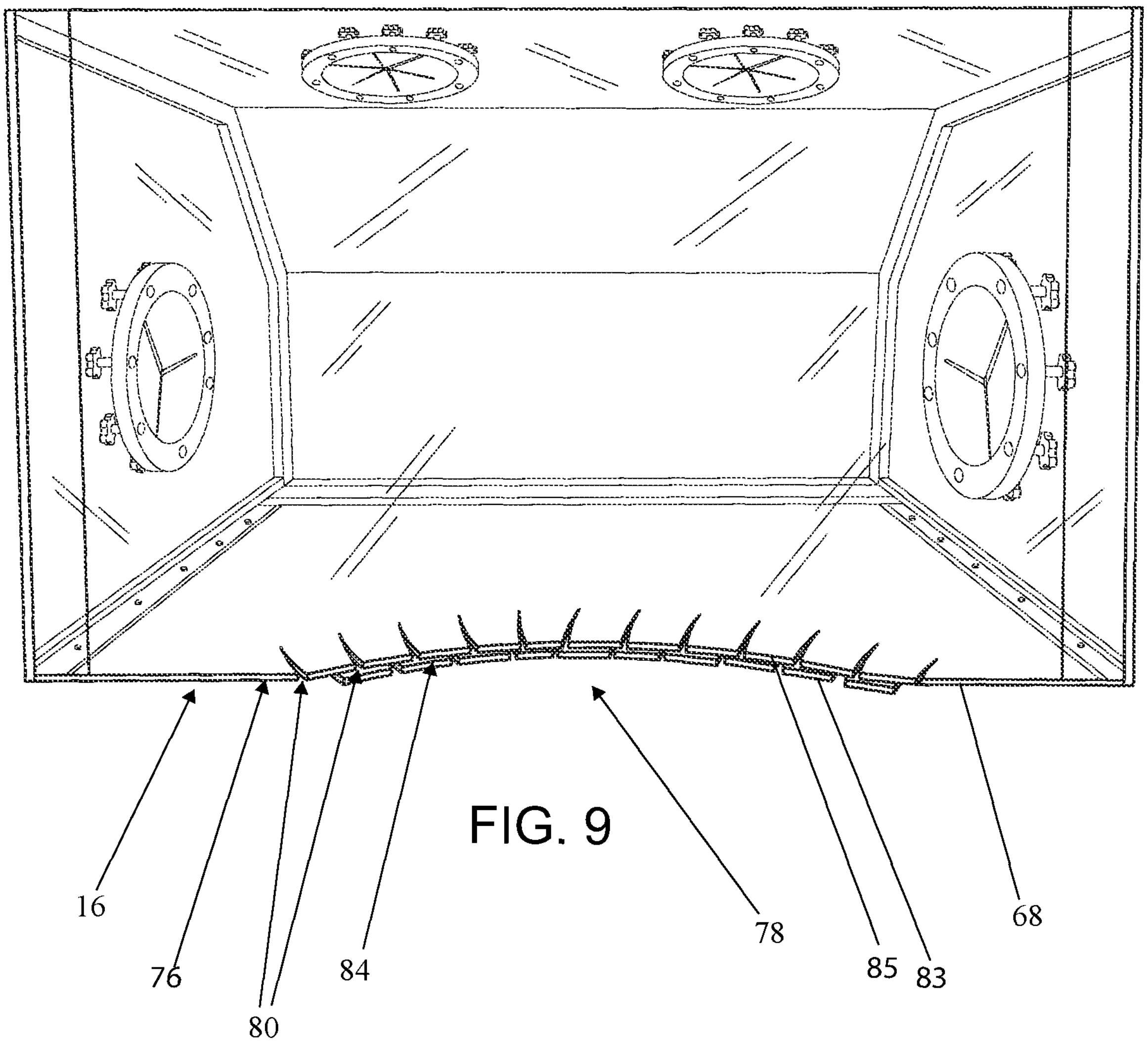
FIG. 9 is a bottom perspective view of the version shown in FIG. 1.
Figure 11:
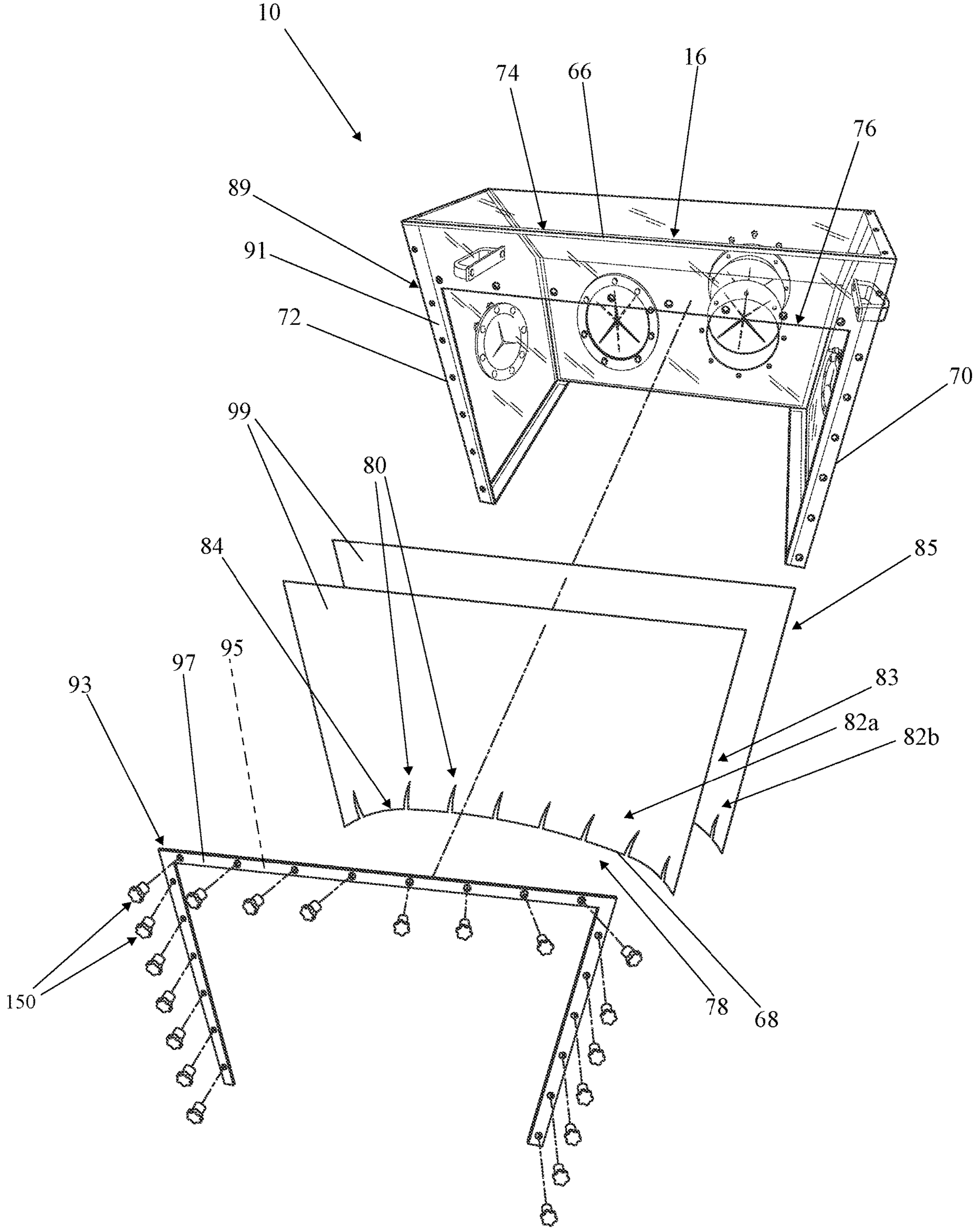
FIG. 11 is a rear perspective view showing an exploded view of the rear patient panel of the version shown in FIG. 1.

As shown in FIG. 8, FIG. 9, and FIG. 11, the example lower patient portal 76 is preferably made of one or more thin layers of flexible sheet inserts, such as rubber, silicone or other elastic material. In the version, a portion of the bottom perimeter 68 of the lower patient portal 76 is arcuate in nature defining the curvature and upper limits of the patient entrance 78. Preferably, the arcuate portion 84 of the bottom perimeter 68 provides a diaphragm style configuration—allowing the bottom perimeter 68 to expand over the patient's 04 upper chest by way of a series of flaps 82 formed between radial divides 80 along the arcuate portion 84.

With reference to FIG. 11, in a version of the application, the lower patient portal 76 may provide two adjacent layered flexible sheet inserts 83, 85. The arcuate portion 84 of the bottom perimeter 68 of each flexible sheet insert 83, 85 comprises a series of flaps 82 formed between radial spaced divides 80. Preferably, the flaps 82*a* of the first flexible sheet insert 83 are operably positioned offset from the flaps 82*b* of the second flexible sheet insert 85. The divides 80 of each flexible sheet insert 83, 85 are staggered to limit portal patency by collapsing and molding around the patient (See FIG. 1). Overall, the collapsible material and structure of the lower patient portal 76 operably molds around the patient's upper chest and lower neck while allowing the provider(s) seamless manual access into the cavity 08 via the portals 34, 36, 58, 60. Preferably, the height of the lower flexible patient portal 76 is approximately 17" to 21", preferably 19" and the width is approximately 21" to 28", preferably 24.5".

In certain versions of the application, the flexible patient portal 76 is operably configured to be attachably removable to the rear patient panel 16. For example, as best illustrated in FIG. 8 and FIG. 11, the rear patient panel 16 further includes an attachment perimeter 89 having an exterior attachment surface 91 and a removable support frame 93 having an interior attachment surface 95 and an exterior surface 97. The removable support frame 93 is operably positioned to support at least a portion of the perimeter 99 of each of the flexible sheet inserts 83, 85 between the interior attachment surface 95 of the support frame 93 and the exterior attachment surface 91 of the attachment perimeter 89. The removable support frame 93 is operably attached to the attachment perimeter 89 via a means of connecting the removable support frame 93 to the attachment perimeter 89. Preferably, the means of connecting is a plurality of knob type screws 150 and a reciprocal ferrule providing a threaded sleeve terminating at a flange. In the version, the knob screws 150 and respective ferrule are positioned along the perimeter of the removable support frame 93. More specifically, the knob screws 150 extend through the removable support frame 93 exterior surface 97 and through the attachment perimeter 89 exterior surface 91, thereby coupling with a respective ferrule anchor brought under tension with the tightening of the knob screw 150 seated therein. Thus, the removable support frame 93 is operably configured to allow for replacement and cleaning of the first and second flexible sheet inserts 83, 85 and to allow additional space to clean and sanitize the interior surfaces from the rear patient panel 16. Preferably, the removable support frame 93 has an approximate width of 1" and the depth of 0.5".

Preferably, the rear patient panel 16 further provides improved visual sight into the cavity 08 by providing a transparent top portion 74, wherein the flexible patient portal 76 extends therebelow.

The left side edge 70 of the rear patient panel 16 and the rear edge 46 of the left side panel 18 form a left, rear edge of the intubation barrier 10. Correspondingly, the right side edge 72 of the rear patient panel 16 and the rear edge 56 of the right side panel 20 form a right rear edge of the intubation barrier 10.

As best shown in FIG. 4, the top roof panel 22 is generally configured to enclose the top of the intubation barrier 10 and allow unobstructed view into the cavity 08. In the version, the top roof panel 22 has a front edge 86, a rear edge 88 and opposing left and right side edges 90, 92. The left side edge 90 and the top edge 38 of the left side panel 18 forms a left side top edge, and the right side edge 92 and the top edge 48 of the right side panel 20 forms a right side top edge of the intubation barrier 10. The rear edge 88 of the top roof panel 22 and the top edge 66 of the rear patient panel 16 form a top rear edge of the intubation barrier 10. Preferably, the top roof panel 22 has a depth between 8"-12", preferably 10" and a width of 25"-30", preferably 27.5".

Figure 5:
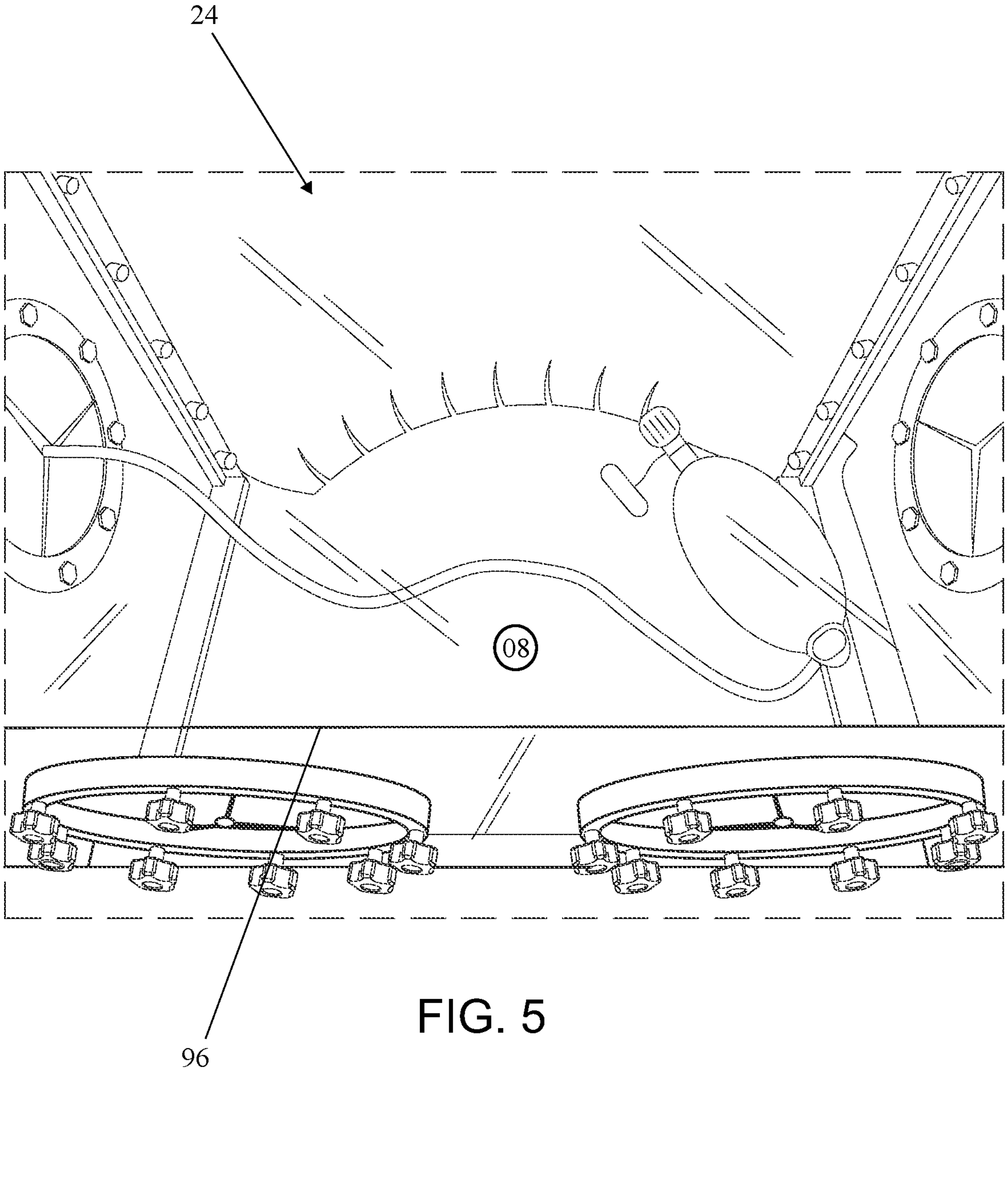
FIG. 5 is an up-close top-down view of the interior cavity of the version shown in FIG. 1.

As best shown in FIG. 4 and FIG. 5, the angled front view panel 24 is generally configured to provide an unobstructed view into the cavity 08 from the perspective viewpoint of the operator—which is positioned above and forward of the intubation barrier 10. The angled front view panel 24 has a top edge 94, a bottom edge 96, and opposing left and right side edges 98, 100 forming a rectangular panel having a plane that is angled relative to and between the plane of the top roof panel 22 and the plane of the front operator panel 14. Thus, providing an unobstructed view from the operator to the patient's head encapsulated within the intubation barrier 10. Preferably, the plane of the angled front view panel 24 is between 30 and 60 degrees, preferably 45 degrees, relative to the bottom perimeter of the intubation barrier 10 or the horizontal axis thereof. Preferably, the angled front view panel 24 has a length between 7"-12", preferably 9.5" and a width of 25"-30", preferably 27.5".

The angled front view panel 24 enhances operator visualization by reducing obstructions and glare and maximizes the necessary proximity of the operator's direct line of sight to the patient's face (See FIG. 4).

The top edge 94 of the angled front view panel 24 and the front edge 86 of the top roof panel 22 form a bend line between the respective panels, and the bottom edge 96 of the angled front view panel 24 and the top edge 26 of the front operator panel 14 form a second bend line between the respective panels. Further, the left side edge 98 of the angled front view panel 24 and the angled edge 42 of the left side panel 18 form a left top angled edge of the intubation barrier 10. Further, the right side edge 100 of the angled front view panel 24 and the angled edge 52 of the right side panel 20 form a right top angled edge of the intubation barrier 10.

Optionally, in certain versions of the application and as best shown in FIG. 3, a bottom perimeter support footing 102 is provided which improves stability of the intubation barrier 10 while positioned over the patient 04 and on the hospital bed 06. More specifically, the bottom perimeter support footing 102 offers physical integrity and support as well as stability on soft, compressible surfaces such as hospital beds (See FIG. 1). The bottom perimeter support footing 102 is generally positioned along the bottom perimeters 28, 40, and 50 of the front operator panel 14, the left side panel 18, and the right side panel 20, essentially the panels that contact the patient's bed 06. The bottom perimeter support footing 102 generally extends inward therefrom defining a rectangular frame which further defines the open bottom 12 of the intubation barrier 10. Preferably, the depth of the support footing is between 1"-5", preferably 2.5". Preferably, the dimensions of the bottom footprint of the intubation barrier 10 or the outer perimeter 21 of the support footing 102 has a width between 25"-30", preferably 27.5" and a length between 14"-19", preferably 16.5". Preferably, the inner perimeter 23 of the support footing 102 has a width between 21.5"-26.5", preferably 24" and a length between 12"-17", preferably 14.5".

Figure 10:
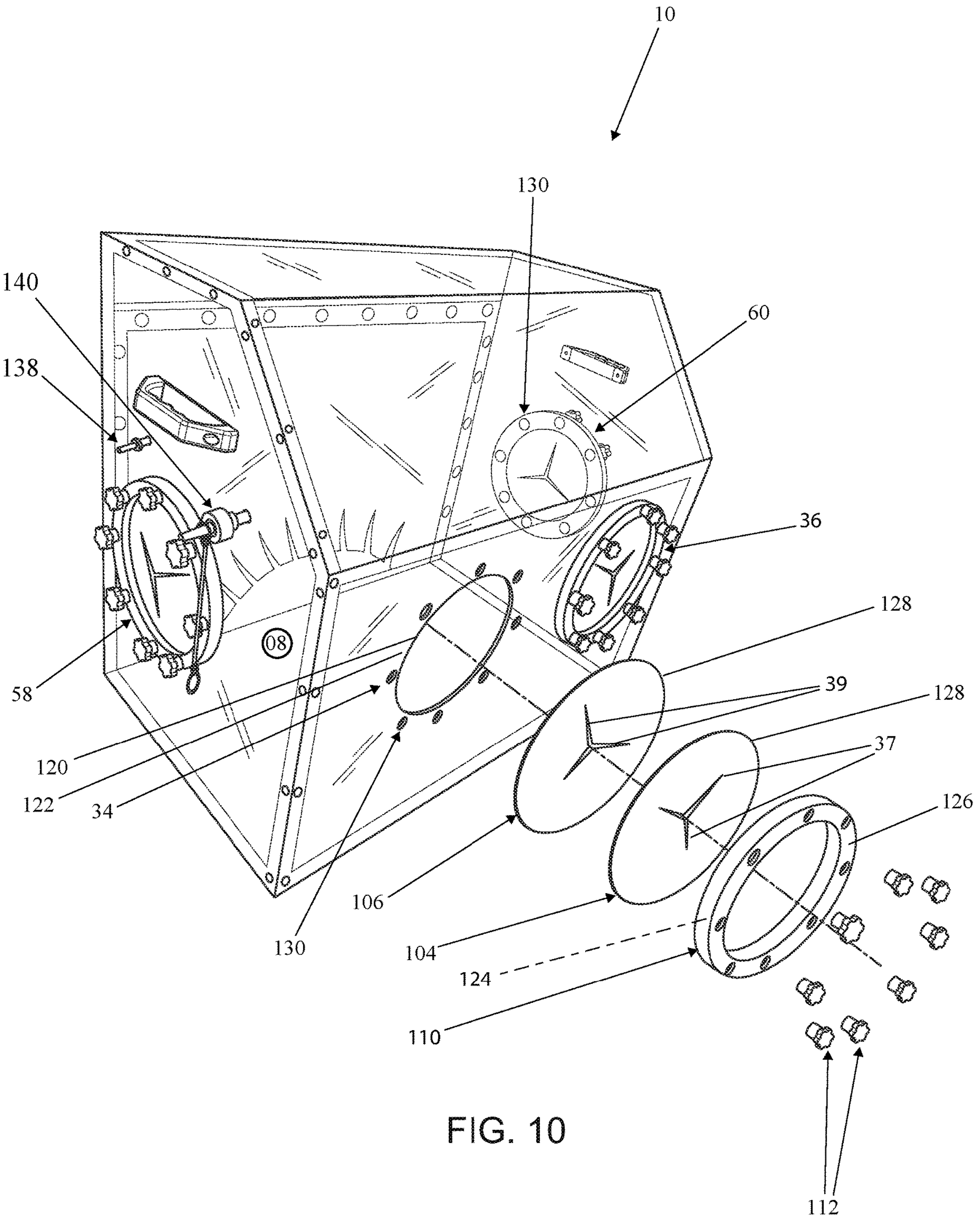
FIG. 10 is a perspective view showing an exploded view of the left operator arm portal of the version shown in FIG. 1.

With reference to FIG. 3 and FIG. 10, the operator arm portals 34, 36 and the assistant arm portals 58, 60 are preferably iris-style diaphragm apertures which operably close in the absence of an arm, forming an enclosure over the portal. In the version, each of the portals comprises at least two adjacent flexible sheet inserts 104, 106, each having a plurality of radial divides 37, 39 emanating from the center and equidistant from the other. Preferably, the flexible sheet inserts 104, 106 are elastic in nature and are manufactured of a rubber or other synthetic material.

In the illustrated version as shown in FIG. 6 and FIG. 10, the first flexible sheet insert 104 and the second flexible insert 106 each comprise three radial divides 37, 39, providing a star or iris configuration. Preferably, the radial divides 37 of the first flexible sheet insert 104 are operably positioned offset from the radial divides 39 of the second flexible sheet insert 106. Preferably, the radial divides 37 of the first flexible insert 104 and the radial divides 39 of the second flexible insert are offset by approximately 60 degrees or, if more than three radial divides, the amount of offset is calculated by dividing 360 degrees by the number n of divides, then divided in half.

Thus, the divides 37, 39 of each flexible sheet insert 104, 106 are staggered from one another to limit portal patency but to also allow seamless manual access in where the flexible sheet inserts 104, 106 collapses and molds around the provider's hands, wrists and forearms (See FIG. 6). Preferably, the internal diameter of the arm portal is between 5"-9", preferably approximately 7". The external diameter of the arm portal (including frame) is preferably between 6.5"-10.5", preferably approximately 8.5". Alternatively, telescoping sleeved gloves may be utilized in lieu of the iris style portal which offers additional exposure protection.

In certain versions of the application, and as referenced by FIG. 10, the diaphragm style portals including the flexible sheet inserts 104, 106, are operably configured to be attachably removable to each respective panel. For example, each portal 34, 36, 58, and 60 further includes an attachment perimeter 120 having an exterior attachment surface 122 and a removable support frame 110 having an interior attachment surface 124 and an exterior surface 126. The removable support frame 110 is operably positioned to support, pinch, or urge the perimeter 128 of the one or more adjacent flexible sheet inserts 104, 106 between the interior attachment surface 124 of the support frame 110 and the exterior attachment surface 122 of the attachment perimeter 120—providing an airtight seal about the perimeter 128 of the adjacent flexible sheet inserts 104, 106. In the illustrated version, the removable support frame 110 is in the shape of a ring.

The removable support frame 110 is operably attached to the attachment perimeter 120 via a means of connecting the removable support frame 110 to the attachment perimeter 120. Preferably, the means of connecting is a plurality of knob screws 112 and reciprocal ferrule 130 providing a threaded sleeve terminating at a flange. In the version, the knob screws 112 and respective ferrule are radially positioned about the exterior surface 126 of the removable support frame 110—specifically, extending through the removable support frame 110 exterior surface 126 and through the attachment perimeter 120 exterior attachment surface 122, wherein the flange of the ferrule 130 anchors under tension while tightened with the knob screw 112 therein. Thus, the removable support frame 110 is operably configured to allow for replacement and cleaning of the first and second flexible sheet inserts 104, 106. Preferably, the removable support frames 110 have an approximate width of 0.75" and a depth of 0.5".

In certain versions, the removable support frame 110 is circular in form corresponding to the size and dimensions of the respective circular flexible sheet inserts 104, 106. Preferably, the first and second flexible sheet inserts 104, 106 are manufactured of rubber or other elastic material. Other dimensions and shapes of the portals are envisioned which would provide a similar operation.

With reference to FIG. 3, preferably, the center 132 of each of the operator arm portals 34, 36 are approximately 7.75"-11.75", more preferably 9.75" from the bottom perimeter 28 of the front operator panel 14 and the center 132 of each of the operator arm portals 34, 36 are approximately 5.75"-9.75", more preferably 7.75" inches from the corresponding left and right side edges 30, 32 of the front operator panel 14. Preferably, the distance between the centers 132 of each of the operator arm portals 34, 36 is spaced approximately 10"-14", more preferably 12" inches from the other.

With reference to FIG. 7, preferably, the center 134 of each of the assistant arm portals 58, 60 are approximately 7.75"-11.75", more preferably 9.75" from the bottom perimeter 40, 50 of each respective left and right side panels 18, 20 otherwise positioned at the same elevation as the operator arm portals 34, 36. Further, preferably the center 134 of each of the assistant arm portals 58, 60 is approximately 7"-12", more preferably 9.75" from the respective left and right side edges 30, 32 of the front operator panel 14.

The rationale for the size and placement of the operator arm portals 34, 36 is intended to maximize dexterity to work with both hands over the patient's 04 head and neck within the interior cavity 08. Similarly, the size and placement of the assistant arm portals 58, 60 are meant to maximize dexterity and flexibility to manually assist over the patient's 04 head and neck.

If the operator is not actively using the operator arm portals 34, 36, an assistant could utilize both the side assistant arm portal 58, 60 as well as the nearest operator arm portal 34, 36 if there is a need for the assistant to have bimanual access to the interior of the box.

The size and placement of portals 34, 36, 58, and 60 for future iterations of intubation barrier boxes can be adjusted for variable functionality not limited to evolving procedures and equipment potentially used within the cavity 08.

In certain versions of the application, as pictured in FIG. 10, one or both of the left side panel and the right side panel 18, 20 may provide support for a suction port 138 and/or an oxygen port 140. The suction port 138 functions as a conduit from the exterior to the interior cavity 08 of the intubation barrier 10. Preferably, a male connector is attached to the left side panel 18 above the assistant arm portal 58 nearer to the front operator panel 14 to accommodate the attachment of suction tubing if negative pressure is desired or required.

The oxygen port 140 also functions as a conduit to the interior cavity 08 embedded through the respective panel of the intubation barrier 10. Preferably, as shown, a male connector is attached to the left side panel 18 above the assistant arm portal 58 near the front operator panel 14 to accommodate the attachment of oxygen tubing if supplemental oxygen is desired.

Further, as shown in FIG. 5, each of the assistant arm portals 58, 60 may function as a conduit for tubing to the interior of the box. Negative pressure created by suction can function to reduce aerosols not only within the intubation barrier 10 itself but also limits the potential for aerosol dissipation once the intubation barrier 10 is removed from the patient 04. Additional negative pressure can also be generated simply by keeping a "Yankauer" suction device in the box for the entirety of the procedure.

The above-described configuration provides many advantages when compared to traditional intubation boxes or barriers. The intubation barrier 10 is designed to seal near-completely and close arm portals 34, 36, 58, and 60 when the portals are not being accessed. When the interior 08 of the intubation barrier 10 is manually accessed by a provider, the portal's elastic configuration functions to collapse and mold around the providers's upper extremities.

As best shown in FIG. 1, once the intubation barrier 10 has been placed over the patient 04, the elastic nature of the arcuate portion 84 of the lower flexible patient portal 76 collapses and molds around the patient's upper chest and lower neck while still allowing for seamless provider access into the interior cavity 08 of the intubation barrier 10.

Further, the intubation barrier 10 geometry is uniquely tailored to provide the best fit for various-sized patients, hospital equipment and substantially improves lowering the exposure to aerosol. For example, the intubation barrier 10 has been configured to fit most critical care stretchers in most emergency departments and intensive care units. If needed, it can be modified and/or augmented to fit smaller stretchers as utilized in operating rooms.

The intubation barrier 10 has been optimally configured to allow the operator to efficiently access the patient's head and neck comfortably given the inherent limitations of fixed access portals in any combination of specific size, shape and spacing. In addition, significant consideration has been made to conceal only the area patient's head and neck down to approximately the top of the shoulders for several reasons: (1) the full range of motion of the upper extremities has been made available to nursing (i.e. peripheral IV, interosseous access, etc.); (2) increase eligibility for use of the box in patients with extremely tall chest girths and/or with very wide shoulders; and (3) leaving the anterior precordium/chest exposed in those instances of cardiac arrest where chest compressions and/or electrical cardioversion might be indicated.

Further, special considerations were made to maximize the interior height of the intubation barrier 10 over the patient's head and neck to accommodate the variable vertical space required and preferred by most operators for most procedures in order to make the intubation barrier 10 most widely and comfortably accepted. The vertical interior cavity 08 above the patient's head and neck is adequate for a variety of procedures not limited to direct laryngoscopy (DL), video-enhanced indirect laryngoscopy, vertical positioning and manipulation of an endotracheal tube or other airway devices/adjuncts, manual ventilation with a bag-valve-mask (BVM) as well as the use of accessories such as a bougie, etc.

The geometry of future generations of the intubation barrier can be adjusted for variable functionality including any new procedures and evolving technology to be used within or as part of the barrier, for extremes in patients' body habitus as well as for adjustments to accommodate different bed and table sizes.

Generally, the intubation barrier 10 can be made in any manner and of any material chosen with sound engineering judgment. Preferably, materials will be strong, lightweight, long-lasting, economical, and ergonomic. Preferably, the intubation barrier 10 is constructed of a resilient material such as metal, plastic, or a composite. Further, it is preferable that the intubation barrier 10 be formed of a unitary continuous plate construction and/or molded into the described configuration.

Preferably, each panel of the intubation barrier 10 is made of a polycarbonate (Lexan), acrylic (Plexiglas) or similar product. Preferably, the arm portal flexible sheet inserts 104, 106 are made of gum rubber or equivalent. Preferably, the arm portal support frames 110 are made of polycarbonate (Lexan) or similar. Preferably, the handles 62, 64 are made of plastic, metal, or equivalent.

The invention does not require that all the advantageous features and all the advantages need to be incorporated into every version of the invention.

Although preferred embodiments of the invention have been described in considerable detail, other versions and embodiments of the invention are certainly possible. Therefore, the present invention should not be limited to the described embodiments herein.

All features disclosed in this specification including any claims, abstract, and drawings may be replaced by alternative features serving the same, equivalent or similar purpose unless expressly stated otherwise.

What is claimed is:

1. An intubation barrier defining a cavity having an open bottom for placement over a patient, the intubation barrier comprising:
- a front operator panel comprising:
  - a left side operator arm portal; and
  - a right side operator arm portal;
  - wherein each of the left side and right side operator arm portals support an iris diaphragm operably closing each portal in the absence of an arm;
- a rear patient panel comprising:
  - a patient portal having an arcuate bottom perimeter forming a patient entrance for positioning the upper chest of the patient therein;
- a left side panel comprising:
  - a left side assistant arm portal supporting an iris diaphragm operably closing the portal in the absence of an arm;
- a right side panel comprising:
  - a right side assistant arm portal supporting an iris diaphragm operably closing the portal in the absence of an arm;
- a top roof panel extending between the rear patient panel and the left side and right side panels; and
- an angled front view panel extending between the front operator panel and the top roof panel, the angled front view panel positioned at an angle relative to the top roof panel and the front operator panel;
- wherein at least one of the arm portals comprises:
  - a first flexible sheet insert and a second flexible sheet insert positioned adjacent to the first flexible sheet insert, each having a plurality of radial divides emanating from a center, the plurality of radial divides of the first flexible sheet insert is operably positioned offset from the plurality of radial divides of the second flexible sheet insert;
  - a removable support frame having an interior surface and an exterior surface, the removable support frame operably positioned to support the first flexible sheet insert and the second flexible sheet insert between the interior surface of the removable support frame and an exterior surface of a respective panel, forming an enclosure over the at least one of the arm portals, thereby allowing the first flexible sheet insert and the second flexible sheet insert to be replaced and cleaned; and a plurality of fasteners connecting the removable support frame to the respective panel.

2. The intubation barrier of claim 1, wherein the removable support frame is in the form of a ring and the plurality of fasteners are knob screws that are radially positioned about the exterior surface of the removable support frame.

3. The intubation barrier of claim 1, wherein the rear patient panel further comprises:

an attachment perimeter having an exterior surface;

a removable support frame having an interior surface and an exterior surface, the removable support frame operably positioned to support at least a portion of the perimeter of the patient portal between the interior surface of the removable support frame and the exterior surface of the attachment perimeter; and a plurality of screws connecting the removable support frame to the attachment perimeter.

4. The intubation barrier of claim 1, wherein the arcuate bottom perimeter of the patient portal comprises a series of flaps formed between radial divides, thereby allowing the arcuate bottom perimeter to expand and seal over the chest of the patient.

5. The intubation barrier of claim 1, wherein the patient portal is comprised of a first flexible sheet insert and a second flexible sheet insert, each having an arcuate bottom perimeter that has a series of flaps formed between radial divides, the flaps of the first flexible sheet insert are operably positioned offset from the flaps of the second flexible sheet insert.

6. The intubation barrier of claim 1, further comprising a support footing extending inward from bottom perimeters of the front operator panel, the left side panel, and the right side panel collectively defining the open bottom of the intubation barrier.

7. The intubation barrier of claim 1, wherein the rear patient panel further comprises a transparent top portion, wherein the patient portal extends below the transparent top portion.

8. An intubation barrier defining a cavity having an open bottom for placement over a patient, the intubation barrier comprising:

a front operator panel comprising:

a left side operator arm portal; and a right side operator arm portal;

wherein each of the left side and right side operator arm portals support an iris diaphragm operably closing each portal in the absence of an arm;

a rear patient panel comprising:

a patient portal having an arcuate bottom perimeter forming a patient entrance for positioning the upper chest of the patient therein;

a left side panel comprising:

a left side assistant arm portal supporting an iris diaphragm operably closing the portal in the absence of an arm;

a right side panel comprising:

a right side assistant arm portal supporting an iris diaphragm operably closing the portal in the absence of an arm;

a top roof panel extending between the rear patient panel and the left side and right side panels; and an angled front view panel extending between the front operator panel and the top roof panel, the angled front view panel positioned at an angle relative to the top roof panel and the front operator panel;

wherein the patient portal is comprised of at least a first flexible sheet insert and a second flexible sheet insert, each having an arcuate bottom perimeter that has a series of flaps formed between radial divides, wherein all flaps of the first flexible sheet insert are operably positioned offset from all flaps of the second flexible sheet insert.

9. An intubation barrier defining a cavity having an open bottom for placement over a patient, the intubation barrier comprising:

a front operator panel comprising:

a left side operator arm portal; and a right side operator arm portal;

wherein each of the left side and right side operator arm portals support an iris diaphragm operably closing each portal in the absence of an arm;

a rear patient panel comprising:

a flexible patient portal having an arcuate bottom perimeter forming a patient entrance for positioning the upper chest of the patient therein;

a left side panel comprising:

a left side assistant arm portal supporting an iris diaphragm operably closing the portal in the absence of an arm; and a left side handle for moving the intubation barrier;

a right side panel comprising:

a right side assistant arm portal supporting an iris diaphragm operably closing the portal in the absence of an arm; and a right side handle for moving the intubation barrier;

a top roof panel extending between the rear patient panel and the left side and right side panels;

wherein at least one of the arm portals comprises:

at least a first flexible sheet insert and an adjacent second flexible sheet insert, each having a plurality of radial divides emanating from a center, the plurality of radial divides of the first flexible sheet insert is operably positioned offset from the plurality of radial divides of the second flexible sheet insert;

a removable support frame having an interior surface and an exterior surface, the removable support frame operably positioned to support the first flexible sheet insert and the second flexible sheet insert between the interior surface of the removable support frame and an exterior surface of a respective panel; and a plurality of screws connecting the removable support frame to the respective panel;

wherein the rear patient panel further comprises:

an attachment perimeter having an exterior surface;

a removable support frame having an interior surface and an exterior surface, the removable support frame operably positioned to urge at least a portion of the perimeter of the flexible patient portal between the interior surface of the removable support frame and the exterior surface of the attachment perimeter; and a plurality of screws connecting the removable support frame to the attachment perimeter.

10. The intubation barrier of claim 9, wherein the arcuate bottom perimeter of the flexible patient portal comprises a series of flaps formed between radial divides, thereby allowing the arcuate bottom perimeter to expand and seal over the chest of the patient.

11. The intubation barrier of claim 10, further comprising a support footing extending inward from bottom perimeters of the front operator panel, the left side panel, and the right side panel, collectively defining the open bottom of the intubation barrier.

12. The intubation barrier of claim 11, wherein the rear patient panel further comprises a transparent top portion, wherein the flexible patient portal extends below the transparent top portion.

13. The intubation barrier of claim 12, further comprising a suction port and an oxygen port embedded through at least one of the left side and right side panels.

14. The intubation barrier of claim 9, wherein the removable support frame is in the form of a ring and the plurality of screws are knob screws that are radially positioned about the exterior surface of the support frame.

* * * * *